United States Patent [19]

Ryu et al.

[11] 4,321,402

[45] Mar. 23, 1982

[54] CARBAMATE PROCESS

[75] Inventors: Ji-Yong Ryu, Ramsey; Krishna K. Rao, Paterson; Ralph J. Spohn, Woodcliff Lake; Robert Drogin, Linden, all of N.J.

[73] Assignee: Exxon Research & Engineering Co., Florham Park, N.J.

[21] Appl. No.: 179,065

[22] Filed: Aug. 18, 1980

[51] Int. Cl.$^3$ ............... C07C 125/065; C07C 125/073
[52] U.S. Cl. ........................ 560/24; 560/25; 260/453 P
[58] Field of Search .................... 560/24, 25

[56] References Cited

U.S. PATENT DOCUMENTS

| | | | |
|---|---|---|---|
| 2,860,166 | 11/1956 | Newcamer et al. | 560/24 |
| 3,029,245 | 4/1962 | Aries | 260/294.9 |
| 3,105,848 | 10/1963 | Lender et al. | 560/25 |
| 4,031,106 | 6/1977 | DelPesco | 260/296 R |
| 4,038,377 | 7/1977 | Washall et al. | 423/510 |
| 4,081,472 | 3/1978 | Tsumura et al. | 260/453 P |

FOREIGN PATENT DOCUMENTS 53-128521 3/1978 Japan.

OTHER PUBLICATIONS

E. S. Wallis et al., Org. Reactions 3, 267 (1946).
H. J. Twichett, Chem. Soc. Rev. 3, 209 (1974).
Organic Chemistry by D. J. Cram and G. S. Hammond, P. 304, McGraw-Hill (1964).
B. Altankirk et al., Synthesized N-chlorobenzamide by using t-butyl hypochlorite with 71% yield, J. Org. Chem. 27, 4532 (1962).

*Primary Examiner*—G. T. Breitenstein
*Attorney, Agent, or Firm*—Roland A. Dexter

[57] ABSTRACT

In the process of producing an aromatic polyisocyanate from a methylated benzene compound having the sequential steps of ammoxidation, hydrolysis, conversion of amide to carbamate, condensation and conversion of polycarbamate ester to polyisocyanate, the improvement of converting said amide to said carbamate in a one-step reaction wherein said amide is reacted with an N-halogenating agent in the presence of alcohol and in a reaction medium having a pH of from neutral to basic and a temperature greater than 40° C.

8 Claims, No Drawings

CARBAMATE PROCESS

FIELD OF THE INVENTION

This invention relates to the production of aromatic polyisocyanates. More particularly, it relates to the preparation of a carbamate intermediate from an aromatic amide in a multireaction step process for obtaining aromatic polyisocyanates from methyl aromatic compounds such as toluene.

DESCRIPTION OF THE PRIOR ART

Polyurethanes fill a very important commercial need in both the flexible and rigid plastic fields. For both the flexible and rigid types, the urethane is the product of the reaction of alcohol and isocyanate. Much effort and time is being spent on developing a means for producing these isocyanates in a less expensive and/or toxic manner. Desirable isocyanates for flexible and rigid plastic applications include methylene bis-(phenyl isocyanate) (hereafter designated as MDI) and polymethylene polyphenyl isocyanate (hereafter designated as PMPPI).

There are two accepted commercial processes for the manufacture of isocyanates such as MDI or PMPPI.

(1) Phosgene technology which can be illustrated as follows:

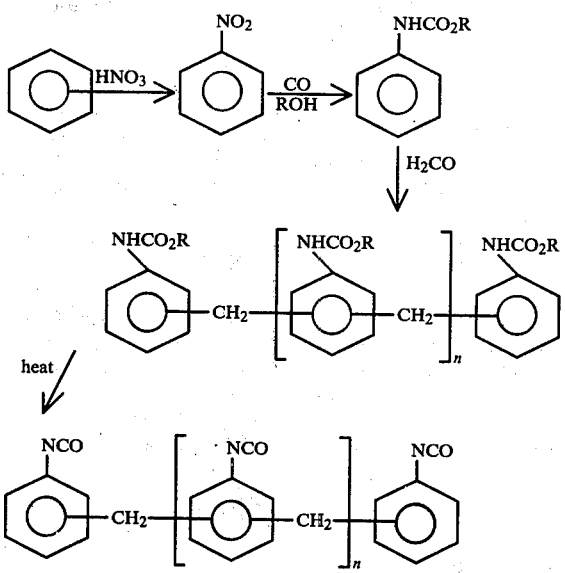

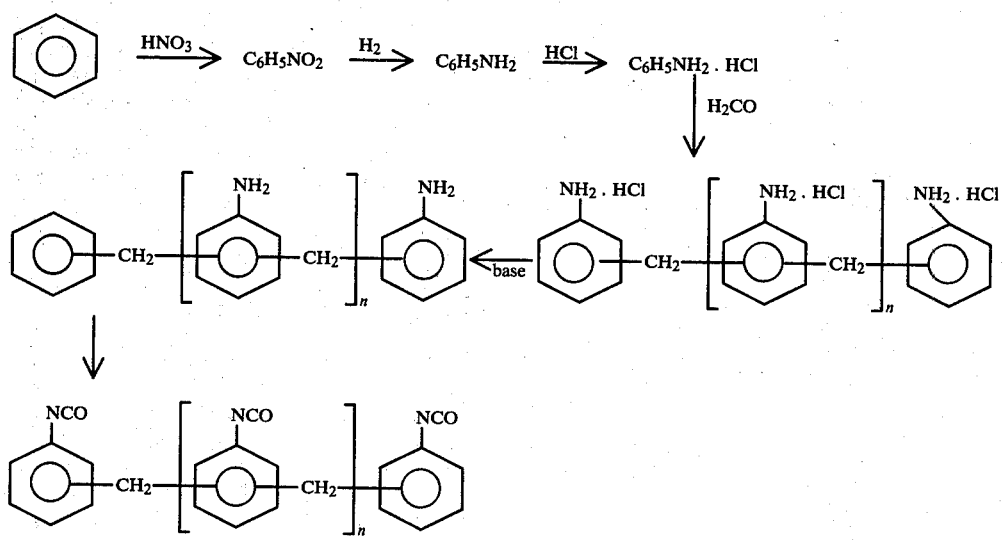

wherein R represents a hydrocarbyl radical such as methyl, and n is the same as before.

wherein n is 0 or an integer ranging from 1 to 5, for the product is generally a mixture of various molecular weight oligomers.

The phosgene approach has some deficiencies including the high toxicity of phosgene gas, poor utilization of reactants and wasteful energy. Nitric acid is manufactured by oxidation of ammonia ($NH_3$) and the aniline is produced by nitration of benzene to nitrobenzene followed by the reduction of nitrobenzene to aniline with $H_2$. One approach to overcoming these drawbacks is to animate the benzene directly with ammonia as is taught in U.S. Pat. No. 4,031,106, but such is not yet commercially useful because of the inefficiency of the amination, even under severe reaction conditions.

(2) Carbonylation technology

In order to overcome some of these deficiencies of the phosgene technology, a carbonylation approach has been developed which may be expressed as follows:

This carbonylation technology is an improvement over the phosgene technology, since it eliminates the use of toxic phosgene gas, HCl and NaOH. However, there are some defects in carbonylation technology which include:

(1) use of more expensive CO in place of hydrogen to reduce the nitro group and hence no material savings, (2) carbonylation of nitrobenzene to carbamate requires high pressure vessels and equipment, (3) use of expensive metal compounds or toxic materials, such as, Se as catalysts, and (4) recycle of unconverted CO to high pressure reactor requires energy.

Because of these defects, which are apparent in the teachings of U.S. Pat. No. 4,038,377 and German DOS No. 2,635,490, the carbonylation technology offers little advantage over a phosgene technology.

It is an object of this invention to overcome many of the defects of the process technology currently used to produce MDI and PMPPI.

SUMMARY OF THE INVENTION

In a copending U.S. patent application, Ser. No. 179,062 filed Aug. 18, 1980 of common assignee, there is described a multireaction step process for the production of aromatic polyisocyanates from methyl aromatic compounds.

The aforesaid process has the following sequential steps: ammoxidation of the methyl group to a nitrile group, hydrolysis of the nitrile group to an amide, conversion of the amide to a carbamate via a Hoffmann rearrangement, condensation with an aldehyde to a polycarbamate, and decomposition of the polycarbamate to a polyisocyanate.

The Hoffmann rearrangement reaction shows that isocyanates can be synthesized from amides by reaction with an N-halogenating agent as hereafter seen:

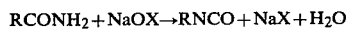

wherein R is the same as before and X represents I, Cl or Br.

Unfortunately, the yield of isocyanates is lower than expected from the above reaction because of the isocyanate hydrolysis:

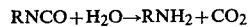

(E. S. Wallis et al., Org. Reactions 3, 267 (1946). Therefore, the Hoffmann rearrangement reaction has to be carried out under anhydrous reaction conditions to obtain high yield of isocyanate (H. J. Twichett, Chem Soc. Rev. 3, 209 (1974)).

In fact, because of this the Hoffmann rearrangement has been primarily used for synthesis of amines. Thus, the art of the N-halogenation of benzamide by the so called Hoffmann reaction using various reagents is very old. For example, the use of bleaching powder, gaseous chlorine and tert-butyl hypochlorite as N-chlorination agents for benzamide were reported in literature as early as, respectively, in 1886 (Ber. 19, 2274), 1922 (JCS 121, p. 203) and 1931 (Chem News 143, p. 265).

Unfortunately, even when anhydrous NaOH is used as base, H$_2$O which can hydrolyze the isocyanate to the amine is produced by reaction of NaOH with reactants or intermediates as shown hereafter:

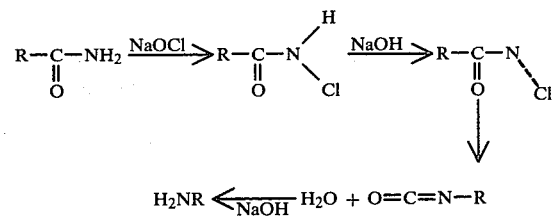

(see Organic Chemistry by D. J. Cram and G. S. Hammond, page 304, McGraw-Hill (1964)). Maintaining anhydrous reaction conditions is too costly for the commercial manufacture of isocyanates.

Even when a Group 1 metal alkoxide is used as a base, formation of by-products, such as ester, cannot be eliminated. However, certain trace by-products as RNClCO$_2$R' are easily expected to be converted to NHCO$_2$R' by heating in the presence of alcohols (R' represents a hydrocarbyl group which may be the same or different than R).

Surprisingly, it has been discovered that the conversion of benzamide to carbamate can be maximized if the reactions are carried out in situ in a specific way. Even if the reactions are carried out in the presence of water, undesirable side reactions can be reduced to minimal, i.e., acceptable levels. This means carbamates can be produced with decreased energy use and maximum utilization of raw materials.

It was found that if the conversion of the amide to carbamate reactions are carried out by maintaining reaction temperatures higher than approximately 40° C., preferably within the range of 45° C. to 100° C., optimally 45° to 90° C., there is significantly less formation of by-products then when the reactions are carried out at 15°–40° C.

It was discovered that if the reactions were carried out while maintaining the reaction medium under neutral to basic conditions, less by-products were produced than reactions carried out under acidic reaction conditions. The pH of the reaction medium ranges broadly from 6 to 12, preferably from 7 to 10. Maintaining the reaction medium under substantially neutral or basic conditions also reduces the corrosivity. If the reactions are carried out under an acidic medium, the reactor corrosion due to halogen acids or halide ions, which originate from N-halogenating agents, will be higher.

It was also found that if the reactions were carried out by adding the N-halogenating agent and base simultaneously to the amide solutions while maintaining reaction temperatures higher than 40° C. and keeping the reaction media basic or neutral, the conversions of amide approached 100%; the formation of by-products were minimal; and, the best utilization of N-chlorinating agents could be obtained. Therefore, separation of unconverted amides and recycle of unconverted amide can be eliminated or substantially reduced.

Better results were obtained when the reactions were carried out with dilute solutions, e.g., benzamide solutions, rather than concentrated solutions. Useful concentrations range from 3 to 40, preferably 5 to 20, weight percent based on amide concentration. Excellent yield and conversion with reasonably dilute solutions are obtainable. It also is expected that if N-halogenating agents, such as t-butyl hypochlorite (hereinafter t-BuOCl) are diluted with suitable diluents, such as t-butyl alcohol or carbon tetrachloride, less by-product formation is expected. t-BuOCl is usually produced by reacting Cl$_2$ with t-butanol in the presence of aqueous NaOH solution. Purification of the product to remove unconverted t-butanol or dehydration of trace water in the product is unnecessary.

By carrying out the reactions in the specific way described above, aqueous NaOH instead of anhydrous NaOH or Group IA alkoxides could be used. Addition of alcohol to the aqueous caustic results in further improvement. Since NaOH is produced by electrolysis of aqueous NaCl solution, sodium hydroxide withdrawn from the cathode compartment can be used without dehydration or purification of crude sodium hydroxide and hence energy requirements and cost of manufacture can be reduced. It was discovered that the addition of NaCl to the aqueous base solution, gave better results.

Since NaCl is produced in a mainly alcohol reaction medium, it can be used to electrolytically produce Cl$_2$ and NaOH without special purification or concentration of NaCl by removal of water, if desired. The recyclability of NaCl to produce NaOH and Cl$_2$ are desired to reduce possible environmental pollution problems.

DETAILED DESCRIPTION OF THE INVENTION

In the aforesaid copending U.S. Application it is taught that most, if not all, of the disadvantages of the prior art processes can be overcome by producing aromatic polyisocyanates, such as MDI and PMPPI, by a multi-step process comprising sequentially ammoxidation of an alkyl aromatic compound, e.g., toluene, hydrolysis of the aromatic nitrile, conversion of the resultant amide to a carbamide, condensation with aldehyde, decomposition of condensation product and recovery of the aromatic polyisocyanate. If desired, ammoxidation of alkyl aromatic compounds can be carried out in two steps, instead of one step, as taught in U.S. Pat. No. 3,029,245.

This new process can be expressed as follows:

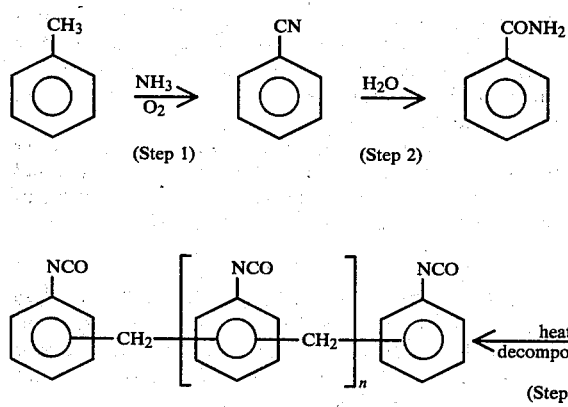

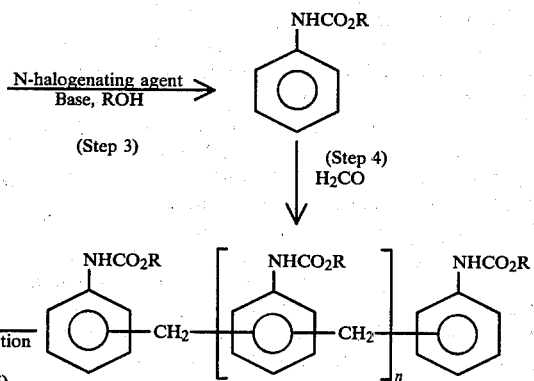

wherein n and R are the same as earlier defined.

As discussed earlier, this new process has 5 essential steps which have been outlined above. The present invention is concerned with an improved means of carrying out Step 3 (above), i.e., the conversion of amide to carbamate. cl Conversion of Amide to Carbamate (Step 3)

This step actually consists of three separate reactions, the improvement of which is the subject matter of this application.

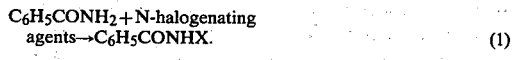

N-halogenating agents are those known generally in the art and include halogens as chloride and bromine, alkyl, and aryl hypohalites, such as t-butyl hypochlorite, t-butyl hypobromite, acetyl hypochlorite and acetyl hypobromite and compounds of the formula M(OX)w wherein M is a group IA or group IIA metal and X is Cl or Br, w is 1 or 2. (B. Altankirk et al synthesized N-chlorobenzamide by using t-butyl hypochlorite with 71% yield, J. Org. Chem., 27, 4532 (1962));

(known as the Hoffmann rearrangement); and

Current practices teach that these reactions must be carried out under anhydrous conditions to achieve high carbamate yield. If these reactions are carried out in the presence of water, a number of undesirable side reactions can occur. For example, if N-chlorination of benzamide is carried out in the presence of water, part of the N-chlorobenzamide formed is decomposed to benzamide. In addition, other undesirable side reactions occur:

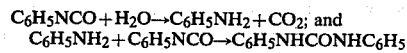

In fact, the Hoffmann hypobromite reaction is used for the preparation of amines, e.g.,

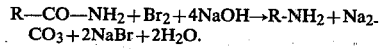

According to the teachings of the art in order to produce isocyanates, the reactions have to be carried out under anhydrous conditions and, hence, Group IA alkoxides, such as sodium methoxide, have been used as the base of the Hoffmann rearrangement.

Application of the Hoffmann rearrangements for the manufacture of isocyanates and arylalkylamines can be found in Japan Pat. No. 54-128521 and France Pat. No. 1,007,001, e.g., n-propyl isocyanate is obtained in 86.7% yield at 97.4% conversion of N-chlorobutyramide by using bi-cyclic amidine as base.

Another serious problem is that the produced benzamide reacts with phenyl isocyanate to form an insoluble precipitate, when the reaction temperatures are below about 40° C.

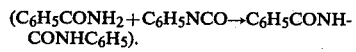

The amide reactant of the process of this invention is an arylamide of the general formula R'(CONH$_2$)$_{n'}$ where R' represents alkaryl or aryl radicals containing 1,2 or 3 rings either condensed or noncondensed and n' is 1, 2 or 3. Representative amides include benzamide (preferred), toluamide, toluenediamide and phthalamide.

In spite of many undesirable side reactions discussed above, it has been discovered that the conversion of amide (said amide can be aryl or alkyl) to carbamate could be achieved in high yield in the presence of water. It was found that the high yields of carbamic acid esters could be obtained by carrying out the three reactions simultaneously, instead of carrying out three reactions in sequence. Reducing the three steps to two steps creates another problem.

When the methyl N-phenyl carbamate is synthesized in two steps by reacting methanolic benzamide solution with t-butyl hypochlorite and then N-chlorobenzamide with methanolic sodium methoxide solution, the undesirable by-product, methyl benzoate, is as high as about 23% of reacted benzamide. (See Example 13).

The preferred technique to carrying out the three reactions simultaneously can be expressed as follows:

1. Simultaneous addition of N-halogenating agents and base solution to benzamide solution. If desired, the base solution, or part of the base solution, can be premixed with the amide solution prior to entering into the reactor.

2. The preferred reaction temperature is approximately higher than 40° C. when methanol is used as the reaction medium. However, the optimum temperatures may be different, depending on the kind of alcohol used to convert the phenyl isocyanate to carbamate. For example, somewhat higher temperature is preferred for ethanol than that for methanol.

3. The preferred solvents for the benzamide solution and the reaction medium are alcohol and mixtures of alcohol with other organic solvents.

4. The dilution of aqueous base solution with organic solvents such as alcohol. Preferred bases are sodium, potassium and lithium hydroxides and trialkyl amines. If the aqueous base solutions are very dilute, i.e. less than about 10 weight percent, addition of MX salts, e.g., NaCl, to base solutions or saturation of base solution with salts is preferred to reduce side reactions in which water is involved directly or indirectly and improve amide conversion. The preferred base contains from 5 to 90, more usefully from 30 to 80, weight percent water.

5. The preferred N-halogenating agents are hypohalites such as t-butyl hypochlorite, sodium hypochlorite, sodium hypobromite, sodium hypoiodite, chlorine, bromine, iodine, $Cl_2O$, $I_2O$ and $Br_2O$. If desired, the N-halogenating agents can be diluted with solvents, such as alcohol, t-butanol or $CCl_4$, or inert gases or solutions of metal hypohalites for use in a large commercial reactor to improve yield and for safety. Since N-halogenating agents are very reactive under the reaction condition, the multiple injection can be employed for large reactor operations.

The use of an alkali or alkaline hypochlorite provides the requisite neutral to alkaline pH reaction conditions, without separate addition of a base though minor amounts can be added for the purpose of stabilizing the hypochlorite solution.

6. The pH of the reaction medium is from neutral to basic. Here, natural means approximately 6 to 8 pH.

7. Rapid mixing of the reactants in the reactor is preferred to reduce undesirable side reactions.

After separation of salt from the reactor effluents, salt is used to regenerate N-halogenating agents, such as tert-butyl hypochlorite via electrolysis.

After removal of solvent and other liquid products from carbamic acid ester, the carbamate is used for the condensation reaction with aldehyde as performed in aforesaid step 4.

The invention will be further understood by reference to the following examples which include preferred embodiments of the invention. However, the examples are not intended to limit the invention of the new process.

EXAMPLE 1

A 250 ml-4-necked micro flask was equipped with an electrically driven one-blade agitator, thermometer, feed inlet and cooling bath. 75 mmoles of benzamide was weighed into the flask and 45 ml of methanol, sufficient to give a 20% solution of amide in solvent, was added along with 6.28 g of 50 wt. % aqueous NaOH solution. Chlorobenzene (12.33 mmoles) was introduced as the internal Gas Chromatographic (hereinafter referred to as GC) standard. t-Butyl hypochlorite (82 mmoles) was pumped into the reactor over a one-hour period. The temperature was maintained at 20° C. and light was excluded from the reactants during this period. Stirring of the reactor was continued for 5 hours. The reactor contained a solid and a liquid phase. The solid was filtered and washed with methanol. The solid cake was washed with additional (40 g) methanol, dried, weighed and analyzed for sodium chloride after dissolution with water. The appearance of insoluble by-product was noted at this point. GC analysis of the filtrate was obtained and product distribution is tabulated in Table I. The water insoluble product was identified as 1-benzoyl-3-phenyl urea by melting point measurement and IR spectra.

By carrying out the reaction in the presence of water at 20° C., only 56.6% selectivity to carbamate and phenyl isocyanate was obtained due to formation of insoluble by-product.

EXAMPLE 2

A 250 ml-4-necked micro flask was equipped with an electrically driven single-blade stirrer, thermometer, feed inlet and bath. 75 mmoles of benzamide was weighed into the flask and 45 ml of methanol, sufficient to give a 20 w/v % solution of amide in solvent was added. Sodium methoxide (80 mmoles) was added cautiously with cooling and chlorobenzene (12 mmoles) was introduced as the GC internal standard. t-Butyl hypochlorite (82 mmoles) was pumped into a stirred reactor over a one-hour period. The temperature was maintained at 20° C. and light was excluded. The temperature was raised to 50° C. with continued stirring for one hour. The reactor on cooling contained a solid and a liquid phase. The solid was filtered off, washed with methanol. The solid filter cake was dried, weighed, and analyzed for sodium chloride after dissolution with water. The aqueous solution was examined for by-product organic material and these were separated to give by-product yield. GC analysis of the filtrate was obtained and the results are hereafter summarized in Table I.

The reaction was carried out at 20° C. under anhydrous reaction conditions by using sodium methoxide as base. The selectivity was improved to 79.5% for this example from 56.6% for Example 1 in which non-anhydrous reaction conditions were employed. The improvement of selectivity in this Example was due to less formation of insoluble by-product. However, methyl benzoate formation was increased.

EXAMPLE 3

This Example is the same as Example 2 except that the reaction temperature was raised to 45° C. and maintained at this temperature for a one-hour post reaction time. The results are summarized in Table I.

This Example shows the reaction temperature effect. By carrying out the reaction at 45° C. instead of 20° C. in Examples 1 and 2, the selectivity improved greatly compared with Example 2, as shown in Table I. The improvement was due to no formation of 1-benzoyl-3-phenyl urea which would form by addition reaction of benzamide to phenyl isocyanate at lower reaction temperature. However, the conversion was slightly lower and another by-product, methyl benzoate, was increased compared with Example 2.

EXAMPLE 4

This Example is the same as described in Example 3 except that the concentration of benzamide was reduced to 10 w/v % from 20 w/v % and the post reaction time was 30 minutes at 45° C. The results are summarized in Table I. Both conversion and selectivity were slightly improved as the reaction was carried out with diluted benzamide solution.

EXAMPLE 5

The equipment and conditions used in this Example are the same as that used in Example 1 except that the temperature was 60° C. to provide a reaction and conditions of 60° C. The results of this Example are summarized in Table I. The NaCl obtained in this Example was dried at 120° C. overnight. This salt contained 300 ppm organic compounds.

This Example shows the effect of water at higher reaction temperature. Although the selectivity was excellent, the benzamide conversion was lower than those of Examples 1 and 3.

EXAMPLE 6

This Example is the same in all respects as that described in Example 5 except that the methanol solvent concentration was increased so as to give a benzamide concentration of 10 w/v %. The post reaction time was 30 minutes at 60° C. The results are summarized in Table I.

This Example shows the effect of the concentration of benzamide solution as aqueous base solution was used. The benzamide conversion was improved.

EXAMPLE 7

Except for a modification in the manner of base addition and the concentration of benzamide, the conditions for this Example are the same as those of Example 6. The benzamide solution was increased to 20 w/v % from 10 w/v % in Example 6. An amount of base solution equivalent to 20% of that required was added to the reaction prior to the simultaneous addition of the t-butyl hypochlorite and the remaining base. The results of this Example are summarized in Table I.

Both conversion and selectivity were excellent despite the presence of water and higher reaction temperature used. The methyl benzoate by-product was approximately one-quarter of that in Example 5. The improvements were due to simultaneous addition of N-chlorinating agent and base to the benzamide solution and maintaining the basic reaction medium during the course of the reaction.

EXAMPLE 8

Except for the dilution of base solution with methanol and post reaction time, the conditions for this Example are the same as those described in Example 7. The amount of methanol ultimately added to the reactor was calculated to give a final concentration of 10 w/v % benzamide in methanol. One-half the methanol was used to prepare the benzamide solution and the other half was used to dilute the aqueous sodium hydroxide solution before it was pumped to the reactor equal to that used in the initial stage of the reaction. There was no post reaction time in this Example. The results are summarized in Table I.

Further improvement of benzamide conversion was made by diluting aqueous NaOH solution with methanol and using further dilute benzamide solution.

EXAMPLE 9

This Example is identical to Example 8 as far as equipment and run conditions except that only a 5% excess of base was used in place of a 10% excess. The results are summarized in Table I.

This Example shows the effect of base concentration in the reaction medium. The conversion in this run was lower than that of Example 8; however, it was higher than that in Example 7.

EXAMPLE 10

The equipment and conditions are the same as those described in Example 8 except for the base solution used. A 90% $H_2O$—10%NaOH solution was used in place of 50% $H_2O$—50%—NaOH solution in the previous Examples. This aqueous NaOH solution was diluted with methanol to provide a 60% aqueous NaOH—40% methanol mixture. The results are summarized in Table I.

This Example shows the effect of water concentration in the base solution. As expected, the conversion was poor. However, surprisingly, the selectivity was good.

EXAMPLE 11

In this Example the solution and equipment was the same as those in Example 10 except that 90% $H_2O$—10%NaOH solution was saturated with NaCl before diluting with methanol. The results are summarized in Table I.

The benzamide conversion was greatly improved compared with that in Example 11 because salt (NaCl) in the base solution. It may be possible to further improve the conversion of the benzamide solution is also saturated with salt. There was no sacrifice of selectivity due to the salt.

EXAMPLE 12

This Example was a duplication of Example 8. The results of all the foregoing examples are summarized in Table I.

TABLE I

| | Example No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Wt. % of B.A.[1] in B.A. Solution | 20 | 20 | 20 | 10 | 20 | 10 | 20 | 10 | 10 | 10 | 10 | 10 |
| Base Used | 50% NaOH –50% H$_2$O | CH$_3$ONa | CH$_3$ONa | CH$_3$ONa | 50% NaOH –50% H$_2$O | 50% NaOH –50% H$_2$O | 50% NaOH –50% H$_2$O | 50% NaOH –50% H$_2$O | 50% NaOH –50% H$_2$O | 10% NaOH –90% H$_2$O | 10% NaOH –90% H$_2$O | 50% NaOH –50% H$_2$O |
| Mode of Base Addition | in sol. with B.A.[1] | in sol. with B.A.[1] | in sol. with B.A.[1] | in sol. with B.A.[1] | in sol. with B.A.[1] | in sol. with B.A.[1] | S.A.[2] | S.A.[2] | S.A.[2] | S.A.[2] | S.A.[2] | S.A.[2] |
| Reaction Time (min.) | 60 | 60 | 60 | 60 | 60 | 60 | 60 | 60 | 60 | 60 | 60 | 60 |
| Reaction Temp. (°C.) | 20 | 20 | 45 | 45 | 60 | 60 | 60 | 60 | 60 | 60 | 60 | 60 |
| Products | | | | | | | | Yield (mmole) | | | | |
| B.A.[1] | 4.97 | 5.40 | 7.48 | 6.58 | 9.20 | 7.20 | 5.30 | 0.38 | 3.70 | 22.5 | 6.76 | 0.74 |
| Phenyl isocyanate | 3.30 | 1.96 | 0.72 | 2.14 | 0.20 | 0.70 | 0.80 | 0.43 | 0.52 | 0.63 | 0.63 | 0.94 |
| Methyl benzoate | 0.41 | 0.64 | 1.49 | 1.04 | 0.70 | 0.30 | 0.20 | 0.23 | 0.38 | 0.51 | 0.20 | 0.61 |
| By-Product (Insoluble) | 12.50 | 7.60 | 0 | 0 | 0 | 0 | 0 | 0 | 0 | 0 | 0 | 0 |
| Carbamate | 29.80 | 59.40 | 58.3 | 56.91 | 44.50 | 59.90 | 61.30 | 66.50 | 54.60 | 41.80 | 50.50 | 69.43 |
| B.A.[1] Conversion (%) | 92.2 | 93.5 | 89.0 | 90.1 | 83.2 | 89.4 | 92.2 | 99.4 | 93.8 | 65.6 | 88.4 | 99.0 |
| Selectivity to Carbamate and phenyl isocyanate | 56.6 | 79.5 | 97.5 | 98.3 | 98.4 | 99.5 | 99.7 | 99.7 | 99.3 | 98.8 | 99.6 | 99.1 |
| Mass Balance of B.A.[1] (Mole %) | 84.3 | 109.7 | 90.3 | 88.5 | 72.5 | 90.4 | 89.8 | 89.7 | 78.6 | 86.9 | 77.1 | 95.2 |

[1] B.A. = Benzamide
[2] S.A. = 80% base was added to the benzamide solution simultaneously with t-BuOCl and 20% base was mixed with the benzamide solution prior to the reaction.

EXAMPLE 13

Benzamide was converted in anhydrous medium to N-phenyl methyl carbamate in two steps. The amide reacted with t-butyl hypochlorite to give the chloroamide which then converted to the carbamate by the addition of methanolic sodium methoxide. Benzamide (290 mmoles) was weighed into a 500 ml-4-necked flask equipped with a single-blade mechanically-driven stirrer, thermometer, and an addition funnel. Methanol (180 ml) was added to give a 20% w/v solution of benzamide in methanol. The room was darkened and the reactor was shielded from light by wrapping it in aluminum foil. t-Butyl hypochlorite (290 mmoles) was added slowly over a 15-minute period. The temperature rose 13° C. during the addition period. Sodium methoxide (290 mmoles) in 100 ml of methanol was then added over a 28-minute period and the temperature rise of 14° C. was recorded. Post reaction was continued for two hours during which time the temperature was allowed to equilibrate to ambient temperature. Stirring was discontinued and the reactor was allowed to stand undisturbed overnight. The reactor was heated to reflux (67° C.) to aid in conversion of unreacted phenyl isocyanate to the carbamate. At the termination of the reaction, the reactor contained two phases, one solid and one liquid. The solid was filtered out, dried and weighed. Analysis of the solid after exclusion of sodium chloride showed that 26.3 mole % of benzamide was converted to high melting (203°–204° C.) insoluble by-product (1-benzoyl-3-phenyl urea). Solution analysis by GC reported as uncorrected area % was as follows:

| Benzamide | 0.5% |
|---|---|
| Carbamate | 73.1% |
| Phenyl Isocyanate | 0.9% |
| Methyl Benzoate | 23.0% |

The following Examples show carbamate formation using sodium hypochlorite with and without the addition of a base.

EXAMPLES 14–25

For all of these Examples, the solution of benzamide (BA), methanol (MeOH), and sodium hydroxide (NaOH) [except when not present in Examples 14, 15, 22 and 23] in water ($H_2O$) was heated to 50° C. at which temperature it was held for 15 minutes during which time sodium hypochlorite was added and thereafter for 20 minutes with agitation.

The amounts of the reactants and the product results are hereafter set forth in Table II. There were no insoluble by-product (such as acyl urea) formation under the reaction conditions reported in Table II.

TABLE II

| Example Nos. | 14 | 15 | 16 | 17 | 18 | 19 | 20 | 21 | 22 | 23 | 24 | 25 |
|---|---|---|---|---|---|---|---|---|---|---|---|---|
| REACTANTS | | | | | | | | | | | | |
| BA (mmol) | 75 | 150 | 75 | 75 | 75 | 75 | 75 | 75 | 75 | 75 | 75 | 75 |
| MeOH (gms) | 100 | 100 | 75 | 100 | 150 | 100 | 100 | 100 | 100 | 100 | 100 | 100 |
| NaOH (mmol) | — | — | 21.5 | 21.5 | 21.5 | 10.8 | 21.5 | 43.0 | — | — | 21.5 | 21.5 |
| $H_2O$ (mmol) | 1392 | 2784 | 549 | 549 | 549 | 783 | 783 | 783 | 1392 | 500 | 500 | 1251 |
| OCl (mmol) | 79* | 158* | 71 | 71 | 71 | 71 | 71 | 71 | 79* | 71 | 71 | 71* |
| Yield (% by G.C.) | | | | | | | | | | | | |
| Methyl Carbamate | 83.7 | 70.5 | 82.7 | 86.1 | 85.4 | 80.0 | 84.3 | 66.3 | 83.7 | 77.2 | 87.3 | 82.7 |
| BA | 6.6 | 17.9 | 5.0 | 5.4 | 3.5 | 9.5 | 5.8 | 5.8 | 6.6 | 14.5 | 1.3 | 6.3 |
| Phenyl Isocyanate | 0.4 | 1.0 | 0.2 | 0.9 | 1.4 | 0.3 | 0.2 | 3.4 | 0.4 | 1.5 | 0.5 | 0.2 |
| Methyl Benzoate | 0.1 | 0.1 | 0.2 | 0.3 | 0.3 | 0.2 | 0.3 | 0.4 | 0.1 | 0.5 | 0.2 | 0.3 |
| Aniline | 5.6 | 6.9 | 9.4 | 5.8 | 6.6 | 8.4 | 7.5 | 19.3 | 5.6 | 3.3 | 6.0 | 9.4 |
| Conversion[1] | 93.4 | 82.1 | 95.0 | 94.6 | 96.5 | 90.5 | 94.2 | 94.2 | 93.4 | 85.5 | 98.7 | 93.7 |
| Selectivity[2] | 90.0 | 87.1 | 87.3 | 92.0 | 90.0 | 88.7 | 89.7 | 74.0 | 90.0 | 92.1 | 89.0 | 89.0 |

*Commercial grade, 20% sodium hypochlorite by volume (16% by weight)
[1] Conversion = 100% − G.C. % BA
[2] Selectivity = $\frac{\text{G.C. \% Methyl Carbamate} + \text{G.C. \% Phenyl Isocyanate}}{100\% - \text{G.C. \% BA}}$ Since the sodium hypochlorite generates basicity to the reaction system simultaneous with the reaction with the amide, it is possible to avoid the separate base addition. Excessive amounts of base can have an adverse effect on carbamate yield. This is shown by a comparison of Ex. 19, Ex. 20 and Ex. 21 where the yield of carbamate was reduced from 90% to 74%. However, a small addition of caustic improves the carbamate yield. In conclusion, the proper amount of base addition gives beneficial effect on carbamate yield.

Although sodium hypochlorite solutions contained large quantities of water, the excellent results could be obtained by carrying out the reaction in the specific manner which is the invention of this disclosure.

The invention in its broader aspect is not limited to the specific details shown and described and departures may be made from such details without departing from the principles of the invention and without sacrificing its chief advantages.

What is claimed is:

1. A process for making N-aryl carbamic acid esters which comprises simultaneously reacting an aryl amide and a N-halogenating agent in the presence of alcohol at a temperature of from about 40° to about 200° C., while maintaining the pH of the resulting reaction medium of from neutral to basic by the addition of an aqueous solution of base said base being selected from the group consisting of NaOH, KOH, LiOH, and tri-alkyl amines, and while continually mixing the reactants for a period of from about 1 minute to 10 hours, and thereafter recovering the carbamate product.

2. A process according to claim 1 wherein said N-halogenating agent is a $C_3$ to $C_5$ alkyl hypochlorite and about a stoichiometric quantity (based on said hypochlorite) of base is present during said reacting.

3. A process according to claim 2 wherein said agent is t-butyl hypochlorite and said base is sodium hydroxide.

4. A process according to claim 1 wherein said N-halogenating agent is a hypochlorite of a Group IA and Group IIA element of the Periodic Table.

5. The process of claim 1, wherein said aryl carbamate acid ester is:

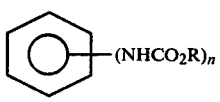

and n is defined as 1, 2 or 3 and R represents a $C_1$–$C_5$ alkyl group.

6. The process of claim 1 wherein said aryl carbamic acid ester is:

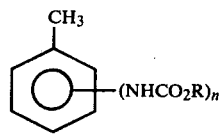

and n is defined as 1, 2 or 3 and R represents a $C_1$–$C_5$ alkyl group.

7. The process according to claim 1 wherein the reaction temperature ranges from 45° to 100° C., and the duration of mixing ranges from 5 minutes to 2 hours.

8. The process of claim 1 wherein the base used for pH control is selected from the group consisting of NaOH, KOH, and LiOH.

* * * * *